United States Patent [19]

Kettner et al.

[11] Patent Number: 4,582,821

[45] Date of Patent: Apr. 15, 1986

[54] INHIBITION OF CYCLIC NUCLEOTIDE INDEPENDENT PROTEIN KINASES

[75] Inventors: Charles A. Kettner, Wilmington, Del.; Efraim Racker, Ithaca, N.Y.

[73] Assignee: E. I. Du Pont de Nemours and Company, Wilmington, Del.

[21] Appl. No.: 552,255

[22] Filed: Nov. 16, 1983

[51] Int. Cl.[4] .................... A61K 37/00; C07C 103/52
[52] U.S. Cl. ................................ 514/18; 260/112.5 R
[58] Field of Search .................... 260/112.5 R; 514/18

[56] References Cited

PUBLICATIONS

Journal of Medicinal Chem. 1977, vol. 20, 452 and 453.
J. Med. Chem. 1980, 23, 275–278.
Biochemistry 1982, 21 6138–6144.
Biochimica et Biophysica Acta 601, 1980, 640–653.
Blaha, et al., "Peptides" (1982) 617–622.
Enzyme Systems Products (1981).
Biochimica et Biophys. Acta 480 (1977) 246–261.
Chemistry and Biochem. of Amino Acid Peptides and Proteins, vol. 4, (1971) Chapter 3.
Sefton, et al., *Cell* 20:807 (1980).
Hunter, *TIBS* 7:246 (1982).
Erikson, et al., *J. Cell. Biol.* 87:319 (1980).
Kasuga, et al., *Proc. Nat. Acad. Sci. USA* 80:2137 (1983).
Cohen, et al., *J. Biol. Chem.* 255:4834 (1980).
Erikson, et al., *J. Biol. Chem.* 256:11381 (1981).
Richert, et al., *Cell* 18:369 (1979).
Weber, *Cell* 5:253 (1975).
Johnson, et al., *Biochemistry* 21:2984 (1982).
Sajadi, et al., *J. Med. Chem.* 23:275 (1980).
Navarro, et al., *Biochemistry* 21:6138 (1982).

*Primary Examiner*—Delbert R. Phillips

[57] ABSTRACT

Peptide and amino acid halomethyl ketones are employed in processes for inhibiting cyclic nucleotide independent protein kinase activity and tumor cell growth.

4 Claims, No Drawings

INHIBITION OF CYCLIC NUCLEOTIDE INDEPENDENT PROTEIN KINASES

A portion of the research relating to this invention was supported by Grant BC-156 from the American Cancer Society and Grants CA-14454 and CA-08964 from the National Cancer Institute, DHHS.

BACKGROUND OF THE INVENTION

The present invention concerns a process for inhibiting cyclic nucleotide independent protein kinase activity and related tumor cell growth.

Protein kinases represent a class of cellular enzymes which function, in a broad sense, as activators or modulators of other cellular proteins. One subclass of protein kinases, termed cyclic nucleotide dependent, requires the presence of cyclic AMP or cyclic GMP for activity. These proteins have been implicated in many aspects of normal cell regulation, and typically phosphorylate target proteins at serine or threonine residues.

A second subclass, termed cyclic nucleotide independent protein kinases, phosphorylate proteins at tyrosine and serine residues. However, tyrosine phosphorylation accounts for only about 0.05% of total protein phosphate in normal cells. By comparison, cellular phosphoserine and phosphothreonine are, collectively, 3000 times more abundant. Sefton, et al., *Cell* 20:807 (1980).

Possible roles for tyrosine phoshorylation in cellular regulation and virus-associated malignant cell transformation have been reviewed by Hunter, *TIBS* 7:246 (1982) and Erikson, et al., *J. Cell. Biol* 87:319 (1980). These authors suggest a link between cell transformation by tumor viruses and the appearance of enhanced tyrosine-specific protein kinase activity. Although increased levels of phosphotyrosine have not been observed for all transforming viruses, at least ten viruses have been associated with this phenomenon. For example, chick fibroblasts transformed by Rous sarcoma virus (RSV) exhibit 6–10 fold increases in cellular phosphotyrosine.

The role and ontogeny of tyrosine phosphorylation in cell transformation by certain tumor viruses is unclear. Tyrosine phosphorylation has been implicated in control of normal cell growth processes involving epidermal growth factor (EGF), platelet-derived growth factor (PDGF), and insulin receptor. See Kasuga et al. *Proc. Nat. Acad. Sci, USA* 80:2137 (1983); Cohen et al., *J. Bio. Chem.* 255:4834 (1980); and Sefton et al., supra. Erikson et al., *J. Biol. Chem.* 256:11381 (1981) describe experiments in which protein kinases observed in normal cells stimulated by EGF, and in tumor cells transformed by RSV, were shown to phosphorylate an identical cellular protein with similar specificity. Thus, it has been theorized that inappropriately elevated levels of tyrosine-phosphorylating activity may contribute to neoplastic growth of transformed cells through phosphorylation of normal growth receptors.

In a search for effective antineoplastic agents, several workers have tested certain chloromethyl ketones and diazomethyl ketones as possible inhibitors of transformation-specific protein kinase activity. Richert et al., *Cell* 18:369 (1979), disclose experiments in which N-α-tosyl-L-lysyl chloromethyl ketone (TLCK) was observed to inhibit in vivo protein phosphorylation activity associated with pp60$^{src}$, an avian sarcoma virus (ASV) gene product linked to fibroblast transformation. Weber, *Cell* 5:253 (1975) had previously reported phenotypic reversion of ASV-transformed cells to normal upon treatment with TLCK.

Johnson et al., *Biochemistry* 21:2984 (1982) describe inhibition of hexokinase and protein kinase activities of Ehrlich ascites tumor cells by a chloromethyl ketone derivative of lactic acid, 2-isobutyl 3-oxo-4-chloro-2-butyl carbonate. Antitumor activity has also been described for certain N-tosyl amino acid diazomethylketones and chloromethyl ketones by Sajadi et al., *J. Med. Chem.* 23:275 (1980). Navarro, et al., *Biochemistry* 21:6138 (1982), disclose inhibition of tyrosine protein kinase activity in certain tumor cell preparations by halomethyl ketone derivatives of amino acids and peptides.

Thus, new methods of inhibiting cyclic nucleotide independent protein kinase activity are of interest to the medical community as new approaches to treatment and control of neoplastic cell growth.

SUMMARY OF THE INVENTION

The present invention provides processes for inhibiting cyclic-nucleotide independent protein kinase activity and mammalian tumor cell growth, comprising administering to a mammal an effective amount of a compound of the formula

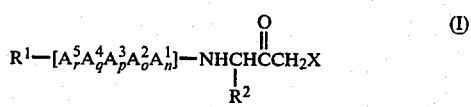

or a physiologically acceptable salt thereof, wherein
R$^1$ is hydrogen or an N-terminal protecting group;
A$^1$ through A$^5$ are amino acid residues, each of which is independently selected from the group consisting of Leu, Tyr, Ala, Phe, Gly, Glu, Lys, Pro, Trp, Arg, Ile, Val, Met, Ser, and Thr;
R$^2$ is methyl, isopropyl, isobutyl, or 4-hydroxybenzyl;
X is Cl or Br; and
n, o, p, q, and r are each 0 or 1.

DETAILED DESCRIPTION OF THE INVENTION

The following abbreviations are employed throughout the specification:
Z: Carbobenzoxy
Boc: t-butyloxycarbonyl
Ac: Acetyl
Bzl: Benzyl ether of serine
All chiral amino acid residues identified herein are of L-configuration, and are abbreviated as follows:
Ala: L-alanine
Arg: L-arginine
Gly: glycine
Glu: L-glutamic acid
Leu: L-leucine
Ile: L-isoleucine
Lys: L-lysine
Met: L-methionine
Phe: L-phenylalanine
Pro: L-proline
Ser: L-serine
Thr: L-threonine
Trp: L-tryptophan
Tyr: L-tyrosine
Val: L-valine In naming compounds useful in the process of the invention, amino acid moiety

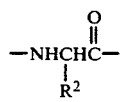

is assigned the name of a corresponding amino acid. Thus, a compound of formula I, above, wherein $R^1$ is Z, $A^1$ is Phe, n is 1, o through r are 0, $R^2$ is isobutyl and X is Cl, is conventionally named N-carbobenzoxy-L-phenylalanyl-L-leucine chloromethyl ketone; this compound is abbreviated herein as Z-Phe-LeuCH$_2$Cl.

As used throughout the specification, "N-terminal protecting group" means an arylcarbonyl, alkylcarbonyl, alkoxycarbonyl, aryloxycarbonyl, aralkoxycarbonyl, arylsulfonyl, alkylsulfonyl, or arylsulfenyl peptide protecting group, or other equivalents known to those skilled in the art of peptide synthesis. Gross and Meienhofer, eds., *The Peptides*, Vol. 3, (Academic Press, New York, 1981) pp. 3–81, the disclosure of which is hereby incorporated by reference, describe numerous suitable amine protecting groups. As used herein, either individually or as part of a larger group, "alkyl" means a linear, cyclic, or branched-chain aliphatic moiety of 1 to 10 carbon atoms; "aryl" means an aromatic moiety, e.g., phenyl, of 6 to 18 carbon atoms, unsubstituted or substituted with one or more alkyl, nitro, alkoxy, or halo groups; and "aralkoxy" means an aryl moiety of 7 to 19 carbons having an aliphatic substituent, and, optionally, other substituents such as one or more alkyl, alkoxy, nitro or halo groups. As used herein, "halo" means F, Cl or Br.

Examples of suitable values for N-terminal protecting group $R^1$ include formyl, acetyl, trifluoroacetyl, benzyloxycarbonyl(carbobenzoxy), substituted benzyloxycarbonyl, tert-butyloxycarbonyl, isopropyloxycarbonyl, allyloxycarbonyl, phthaloyl, benzoyl, acetoacetyl, chloroacetyl, phenoxycarbonyl, p-methoxybenzenesulfonyl, p-toluenesulfonyl, methanesulfonyl and phenylthio. Particularly convenient values for $R^1$ are carbobenzoxy (Z), tert-butyloxycarbonyl (Boc) and acetyl (Ac).

Contemplated classes of compounds useful in various embodiments of the invention include the following. A first class includes compounds of formula I wherein $R^1$, $R^2$ and X are as previously defined, and n through r are each 0. A second class includes compounds of formula I wherein $R^1$, $R^2$ and X are as previously defined; n is 1; o and p are 0 or 1; q and r are 0; and $A^1$ through $A^3$ are independently selected from the group consisting of Phe, Gly, Ala, Glu, Pro, Leu, Lys and Ser. A third class includes compounds of formula I wherein n is 1; o and p are 0 or 1, q and r are 0; $A^1$ is Phe, Ser, Leu, Lys or Ala; and $A^2$ and $A^3$ are independently Phe, Gly, Ala, Glu, Pro, Leu, Lys or Ser.

Contemplated subclasses within each of the foregoing classes include compounds wherein $R^1$ is Z, Boc, or Ac; and compounds wherein $R^2$ is isobutyl or 4-hydroxybenzyl.

On the basis of superior cyclic nucleotide independent protein kinase inhibitory capacity, or superior tumor cell line growth-inhibiting capacity, those compounds of formula I wherein $R^2$ is isobutyl or 4-hydroxybenzyl; n, o and p are independently 0 or 1; q and r are 0, and $A^1$, $A^2$ and $A^3$ are independently selected from the group consisting of Phe, Gly, Ala, Glu, Pro, Leu, Lys and Ser are preferred compounds for use in the process of the present invention. Of the foregoing, those compounds wherein n, o, p, q and r are each 0, and $R^2$ is isobutyl or 4-hydroxybenzyl; and those compounds wherein $R^2$ is isobutyl; $A^1$ is Phe, Ser, Leu, Lys or Ala; $A^2$ and $A^3$ are independently Phe, Gly, Ala, Pro, Lys or Ser; X is Cl; n, o and p are each 1; and q and r are each 0 are particularly preferred.

Specific examples of compounds useful in various embodiments of the invention include
Boc-LeuCH$_2$Br;
Boc-LeuCH$_2$Cl;
Boc-TyrCH$_2$Cl;
Boc-TyrCH$_2$Br;
Boc-ValCH$_2$Cl;
Z-Phe-Gly-Leu-LeuCH$_2$Cl;
Z-Phe-Ser-Ala-LeuCH$_2$Cl;
Z-Phe-Gly-Ala-TyrCH$_2$Cl;
Z-Phe-Gly-Ser-LeuCH$_2$Cl;
Ac-Phe-Gly-Ala-LeuCH$_2$Cl;
Z-Phe-Gly-Ala-LeuCH$_2$Cl;
Z-Phe-Gly-Phe-LeuCH$_2$Cl;
Z-Phe-Leu-Ala-LeuCH$_2$Cl; and
Z-Phe-Gly-Lys-LeuCH$_2$Cl.

Physiologically acceptable salts of compounds of formula I include acid addition salts of free base, if present, wherein the acid can be organic or inorganic, e.g., hydrochloric, phosphoric, maleic, acetic, citric, succinic, etc. Alternatively, salts of free peptidic acids, including sodium, potassium, and ammonium salts, are included within the scope of compounds useful in the present invention.

In practicing the process of the invention, the foregoing compounds can be employed alone, in combination with one another or with other chemotherapeutic agents, and/or in combination with various inert pharmaceutically acceptable carriers in a variety of dosage forms, orally or parenterally. Dose requirements will vary with the compound and dosage form employed and the animal being treated. Typically, therapy is initiated at lower dosages and dosage is increased until the desired inhibiting effect is achieved.

The compounds employed in the invention can be prepared by techniques generally corresponding to those disclosed by Kettner et al., *Arch. Biochem. Biophys.* 162:56 (1974).

First, N-protected peptides or amino acids are reacted with about one equivalent of N-methylmorpholine and one equivalent of isobutyl chloroformate at about −20° C., generating a mixed peptide-isobutyric acid anhydride. This standard technique is described by Anderson et al., *J. Amer. Chem. Soc.* 89:5012 (1967). Second, the mixed anhydride is treated with about one equivalent of diazomethane in tetrahydrofuran or other suitable inert, aprotic solvent at 0° C., generating an N-protected peptide or amino acid diazomethyl ketone. Third, the latter compound is treated with a solution of HCl or HBr in anhydrous ethanol or ether at 0° C., producing an N-protected halomethyl ketone.

Larger peptide halomethyl ketones can be assembled by repetitively coupling a deprotected halomethyl ketone to mixed anhydrides of other N-protected peptides or amino acids generated according to the foregoing procedure. Deprotection of N-terminal amino groups can be accomplished by treatment with anhydrous HF or trifluoroacetic acid, or by other methods known to those skilled in the art.

Detailed disclosure of procedures suitable for producing specific compounds useful in practicing the present invention can be found preceding the Examples set forth below. In the preparative procedures and Examples, all parts and percentages are by weight, and all degrees are Celsius, unless otherwise noted.

SYNTHESIS OF PEPTIDE HALOMETHYL KETONES

A. Boc-LeuCH$_2$Br

This compound was prepared substantially according to the procedure of Kettner et al., *Arch. Biochem. Biophys.* 162:56 (1974).

B. Boc-Leu-CH$_2$Cl

Starting material Boc-LeuCHN$_2$ was prepared substantially according to the procedure of Kettner et al., supra.

Boc-LeuCHN$_2$ (4.40 g, 17.2 mmoles) was dissolved in 50 mL of ether and cooled to 0°; anhydrous 3.45N ethanolic:HCl (5.22 mL, 18.0 mmoles) was added. After about 5 minutes, the resulting solution was washed with cold water, saturated aqueous sodium chloride, and was dried over anhydrous sodium sulfate. Solvent was evaporated to yield crystalline Boc-LeuCH$_2$Cl. Product was isolated and washed with petroleum ether to yield 0.84 g (mp 65°–66°) in a first crop and 1.94 g (mp 64°–65.5°) in a second crop isolated from cold petroleum ether.

Anal. Calcd. for C$_{12}$H$_{22}$NO$_3$Cl: C, 54.63; H, 8.42; N, 5.31. Found: C, 54.45, H, 8.13; N, 5.38.

C. Boc-TyrCH$_2$Cl

Boc-TyrCHN$_2$ was prepared by dissolving Boc-TyrOH (10 g, 35.5 mmoles) in 30 mL of tetrahydrofuran and reacting it with N-methylmorpholine (3.91 mL, 35.5 mmoles) and isobutyl chloroformate (4.62 mL, 35.5 mmoles) for 5 minutes at −20°. The resulting reaction mixture was filtered, and precipitate was washed with 50 mL of cold tetrahydrofuran. Filtrate was added to 150 mL of diazomethane:ether (~40 mmoles) and this reaction mixture was stirred for 15 minutes at 0°. Solvent was evaporated with a stream of nitrogen, leaving a residue, which was dissolved in ethyl acetate. The resulting solution was washed with water and saturated aqueous sodium chloride, dried over sodium sulfate, and then solvent was evaporated to yield a crude product. This material was chromatographed on a 4 cm column containing 75 g of silica gel, using chloroform as a solvent, to yield 3.67 g of Boc-TyrCHN$_2$. Product crystallized from ether to yield 1.86 g (mp 136°–137°) in a first crop and 0.58 g (mp 133.5°–134.5°) in a second crop. NMR in CDCl$_3$ indicated the diazo proton at δ5.27.

Anal: Calcd for C$_{15}$H$_{19}$N$_3$O$_4$: C, 58.99; H, 6.28; N 13.76. Found: C, 59.08; H, 6.16; N, 13.65.

Boc-TyrCHN$_2$ (1.81 g, 5.92 mmoles) was dissolved in 30 mL of tetrahydrofuran, and the resulting solution was treated with 3.45N ethanolic HCl (1.72 mL, 5.92 mmoles) for 5 minutes at 0°. Solvent was removed by evaporation on a rotary evaporator without temperature regulation. The resulting residue was dissolved in ethyl acetate, and this solution was washed with 0.2N hydrochloric acid and saturated sodium chloride. The solution was dried over sodium sulfate, and solvent was evaporated to yield crystalline Boc-TyrCH$_2$Cl. The crystals were isolated and washed with cold ether to yield 0.45 g (mp 110°–112°). In a second crop, 0.90 g (mp 110°–112°) was obtained. NMR in CDCl$_3$ corresponded to that expected, except that methylene protons of —COCH$_2$Cl appeared as a doublet at δ4.1.

Anal: Calcd. for C$_{15}$H$_{20}$NO$_4$Cl: C, 57.41, H, 6.44; N, 4.46. Found: C, 57.66; H, 6.66; N, 4.52.

D. Boc-TyrCH$_2$Br

Boc-TyrCHN$_2$ (0.40 g, 1.32 mmoles) was dissolved in 20 mL of tetrahydrofuran, and the resulting solution was cooled to about −10°. Anhydrous HBr: ether (2.3M, 0.58 mL, 1.3 mmoles) was added, and after about 5 minutes, solvent was evaporated, leaving a residue. The residue was dissolved in ethyl acetate, and the resulting solution was washed with water and saturated aqueous sodium chloride. The solution was then dried over anhydrous sodium sulfate and ethyl acetate was evaporated, yielding an oil. The oil was applied to a 2 cm column containing 10 g of silica gel, and the column eluted with chloroform. Eluate solvent was evaporated, and the remaining residue was triturated with hexane to yield crystalline Boc-TyrCH$_2$Br (0.22 g, mp 109.5°–111°).

Anal: Calcd. for C$_{15}$H$_{20}$NO$_4$Br: C, 50.28; H, 5.64; N, 3.91. Found: C, 50.12; H, 5.70; N, 3.78.

E. Z-Phe-Gly-Leu-LeuCH$_2$Cl

H-LeuCH$_2$Cl.HCl was prepared substantially according to the procedure of Kettner et al., *Arch. Biochem. Biophys.* 165:739 (1974).

A mixed anhydride of Z-Phe-Gly-Leu-OH (1.05 g, 2.24 mmoles) was prepared by dissolving this peptide in 10 mL of tetrahydrofuran, cooling the resulting solution to −20°, and adding N-methylmorpholine (0.25 mL, 2.24 mmoles) and isobutyl chloroformate (0.29 mL, 2.24 mmoles). The resulting mixture was stirred for 5 minutes at −20°, 20 mL of cold tetrahydrofuran and triethylamine (0.31 mL, 2.24 mmoles) were added, and this mixture was added to H-LeuCH$_2$Cl.HCl (0.48 g, 2.24 mmoles) dissolved in 5 mL of cold N,N-dimethylformamide. The ensuing reaction mixture was stirred for 1 hour at −20°, and 2 hours at about 23°. The mixture was then filtered, and tetrahydrofuran was evaporated from the resulting filtrate, leaving a residue. The residue was diluted with 100 mL of ethyl acetate, and this solution was washed with 0.2N hydrochloric acid, 5% sodium bicarbonate solution, and saturated aqueous sodium chloride. The solution was dried over anhydrous sodium sulfate and solvent was evaporated to yield 1.2 g of a foam. Product was crystallized from ethyl acetate to yield 0.94 g (mp 160°–161.5°) of Z-Phe-Gly-Leu-LeuCH$_2$Cl.

Anal: Calcd. for C$_{32}$H$_{43}$N$_4$O$_6$Cl: C, 62.47; H, 7.06; N, 9.11. Found: C, 62.32; H, 6.90; H, 9.14.

Additional peptide chloromethyl ketones were prepared by coupling an appropriate N-protected tripeptide to H-LeuCH$_2$Cl, using a procedure substantially similar to that described for Z-Phe-Gly-Leu-LeuCH$_2$Cl, above. In preparing Ac-Phe-Gly-Glu-LeuCH$_2$Cl and Ac-Phe-Glu-Ala-LeuCH$_2$Cl, (Examples 22,23) glutamic acid side chain carboxyl groups were protected as benzyl esters, which were subsequently removed by treatment with anhydrous HF. In preparing Z-Phe-Gly-Lys-LeuCH$_2$Cl and Z-Phe-Lys-Ala-LeuCH$_2$Cl (Examples 30, 31), lysine side chain amino groups were protected by attachment of Boc groups, which were subsequently removed by treatment with anhydrous trifluoroacetic acid.

F. Z-Phe-Ser-Ala-LeuCH$_2$Cl

Z-Phe-Ser(Bzl)-Ala-LeuCH$_2$Cl was prepared by coupling Z-Phe-Ser(Bzl)-Ala-OH (1.37 g, 2.5 mmoles) to H-LeuCH$_2$Cl.HCl by a mixed anhydride coupling procedure substantially analogous to that used for the preparation of Z-Phe-Gly-Leu-LeuCH$_2$Cl in Procedure E. Product was obtained as a crystalline solid, 0.98 g (mp 167°–168°).

Anal: Calcd. for C$_{37}$H$_{45}$N$_4$O$_7$Cl: C, 64.09; H, 6.56; N, 8.08. Found: C, 64.22; H, 6.38; N, 8.08.

Z-Phe-Ser(Bzl)-Ala-LeuCH$_2$Cl (0.71 g, 10.2 mmoles) was treated with a mixture of 15 mL of anhydrous HF and 1 mL of anisole in a commercial HF apparatus (Peptide Institute, Inc.). After 70 minutes at 0°, HF was removed by evaporation and the resulting residue was dried in vacuo over potassium hydroxide overnight. H-Phe-Ser-Ala-LeuCH$_2$Cl.HF, 0.35 g, was obtained after triturating the residue with ether.

H-Phe-Ser-Ala-LeuCH$_2$Cl.HF (0.39 g, 0.71 mmole) was dissolved in a mixture of 2 mL water and 1 mL of dioxane. This solution was cooled to 0° and carbobenzoxychloride (0.10 mL, 0.71 mmole) and sodium bicarbonate (0.12 g, 1.42 mmoles) were added. After 30 minutes at 0°, no ninhydrin positive material could be detected. The resulting mixture was diluted with ethyl acetate and the resulting organic layer was washed with 5% sodium bicarbonate solution, 0.2N hydrochloric acid, and saturated sodium chloride. The solution was dried over sodium sulfate and solvent was evaporated, leaving a residue, which was diluted by 50% with hexane to yield 0.13 g of Z-Phe-Ser-Ala-LeuCH$_2$Cl (mp 155°–157°).

Anal: Calcd. for C$_{30}$H$_{39}$N$_4$O$_7$Cl: C, 59.73; H, 6.53; N, 9.29. Found: C, 59.81; H, 6.47; N, 9.13.

G. Z-Phe-Gly-Ala-TyrCH$_2$Cl

Boc-TyrCH$_2$Cl (0.5 g) (Procedure C) was deprotected by treatment with 20 mL of 3.5N ethanolic HCl for 30 minutes at about 23°. Solvent was evaporated and the resulting product, H-TyrCH$_2$Cl.HCl (0.45 g), was dried in vacuo over solid potassium hydroxide and phosphorus pentoxide.

Z-Phe-Gly-Ala-OH (0.77 g, 1.80 mmoles) was coupled to H-TyrCH$_2$Cl.HCl by a mixed anhydride coupling procedure substantially similar to that used for the preparation of Z-Phe-Gly-Leu-LeuCH$_2$Cl in Procedure E. Product was crystallized from ethyl acetate to yield 0.73 g of Z-Phe-Gly-Ala-TyrCH$_2$Cl, which slowly decomposed from 140°–160° and melted with complete decomposition at 160°–160.5°.

Anal: Calcd. for C$_{32}$H$_{35}$N$_4$O$_7$Cl: C, 61.67; H, 5.67; N, 8.99. Found: C, 61.60; H, 5.92; N, 8.69.

H. Z-Phe-Gly-Ser-LeuCH$_2$Cl

Z-Phe-Gly-Ser(Bzl)-OH (1.21 g, 2.27 mmoles) was coupled to H-LeuCH$_2$Cl.HCl by a mixed anhydride coupling procedure substantially similar to that used for preparation of Z-Phe-Gly-Leu-LeuCH$_2$Cl in Procedure E. The resulting protected product, Z-Phe-Gly-Ser(Bzl)-LeuCH$_2$Cl, was crystallized from ethyl acetate to yield 1.1 g (mp 152.5°–153.5°) of purified product.

Anal: Calcd. for C$_{36}$H$_{43}$N$_4$O$_7$Cl: C, 63.65; H, 6.39; N, 8.25. Found: C, 63.48; H, 6.43; N, 8.08.

Z-Phe-Gly-Ser(Bzl)-LeuCH$_2$Cl (0.98 g, 1.44 mmoles) was treated with anhydrous HF by a method substantially similar to that described for preparation of H-Phe-Ser-Ala-LeuCH$_2$Cl.HF in Procedure F, yielding a hydrofluoride salt, H-Phe-Gly-Ser-LeuCH$_2$Cl.HF (0.69 g).

H-Phe-Gly-Ser-LeuCH$_2$Cl.HF (0.59 g, 1.24 mmoles) was reacted with carbobenzoxychloride (0.18 mL, 1.24 mmoles) and sodium bicarbonate (0.21 g, 2.5 mmoles) in a solution consisting of 3 mL of water and 3 mL of dioxane in an ice bath. After all reagents had been added, the resulting solution was warmed to about 23° and stirred for 30 minutes. Additional sodium bicarbonate (0.10 g, 1.2 mmoles) and carbobenzoxychloride (0.18 mL, 1.24 mmoles) were added and the resulting reaction mixture was stirred for an additional 30 minutes. Another equivalent of carbobenzoxychloride was added, and the reaction was completed as determined by disappearance of ninhydrin positive material. The resulting mixture was diluted to 50 mL with water, and product was extracted into ethyl acetate. The organic layer was washed with 0.2N hydrochloric acid, 5% sodium bicarbonate, and saturated sodium chloride.

Solvent was evaporated to yield a crystalline product, which was washed with ether and then recrystallized from ethyl acetate:hexane to yield Z-Phe-Gly-Ser-LeuCH$_2$Cl (0.28 g, mp 146°–146.5°).

Anal: Calcd. for C$_{29}$H$_{37}$N$_4$O$_7$Cl: C, 59.12; H, 6.34; N, 9.51. Found: C, 59.45; H, 6.36; N, 9.46.

I. Z-AlaCH$_2$Cl

Z-AlaCH$_2$Cl was prepared substantially according to the procedure disclosed by Powers et al., *Biochemistry* 12:4767 (1973).

J. Ac-Phe-Gly-Ala-LeuCH$_2$Cl

Ac-Phe-Gly-Ala-LeuCH$_2$Cl was prepared by a procedure substantially similar to that disclosed by Powers et al., *Biochem. Biophys. Acta.* 480:246 (1977).

K. Boc-ValCH$_2$Cl

Boc-ValCHN$_2$ was prepared by a procedure substantially similar to that described for preparation of Boc-TyrCHN$_2$ (Procedure C) except that Boc-Tyr-OH was replaced with Boc-Val-OH. Boc-ValCHN$_2$ was treated with 3.45N ethanolic:HCl, as described in Procedure C, to give Boc-ValCH$_2$Cl. After crystallization from hexane, product melted at 70°–73°.

Anal: Calcd. for C$_{11}$H$_{20}$NO$_3$Cl: C, 52.89; H, 8.09; N, 5.61. Found: C, 53.19; H, 8.17; N, 5.82.

EXAMPLES 1–15

Inhibition of Epidermal Growth Factor-Mediated Protein Phosphorylation

The capacity of certain peptide halomethyl ketones to inhibit protein phosphorylation is illustrated by Examples 1–8, below, in which solubilized plasma membranes prepared from A-431 human epidermoid carcinoma cells were incubated with [$\gamma$-$^{32}$P] ATP in the presence of EGF.

A-431 human epidermoid carcinoma cells were grown in Dulbecco's modified Eagle's medium containing 5% fetal calf serum. Plasma membranes were isolated by a method substantially similar to that described by Thom et al., *Biochem J.* 168:187 (1977), and kept at −70°. Solubilization of plasma membranes was performed substantially as described by Cohen et al., *J. Biol. Chem.* 255:4834 (1980). In this procedure, 7.5 mg/mL protein was solubilized with 5% Triton X-100 (octylphenol), 10% glycerol, and 20 mM Hepes buffer (N-2-hydroxyethylpiperazine-N$^1$-2-ethanesulfonic acid), pH 7.4. This mixture was incubated for 20 minutes at about 23°, followed by centrifugation at 100,000 xg for 60 minutes.

Protein phosphorylation assays were conducted substantially as described by Carpenter et al., *J. Biol. Chem.* 254:4884 (1979). Each assay mixture contained, in a final volume of 70 μL: 20 mM Hepes, pH 7.4, 0.01% bovine serum albumin (BSA), 15-150 μg protein in Triton extract, 100 ng EGF, 1 mM $MnCl_2$ and 10-20 μM [γ-$^{32}$P] ATP (2-4 μCi). Peptide halomethyl ketones were added as solutions in ethanol; an equivalent volume of ethanol was added to controls. Assay mixtures were incubated at about 23° for ten minutes, with or without added EGF. Mixtures were then held at 0° for ten minutes before initiation of phosphorylation by addition of 15 μM γ-$^{32}$P) ATP (2 μCi). Reactions were terminated after 3 minutes at 0° by applying an aliquot of the assay mixture to a Whatman 3MM filter paper (2×2 cm), which was then suspended in ice-cold 10% trichloroacetic acid containing 10 mM pyrophosphate. This suspension was gently shaken for a period of 1 hour, during which the trichloroacetic acid/pyrophosphate mixture was changed three times. Finally, the filter papers were dried and radioactivity measured by scintillation counting. The results of these experiments are set forth in Table 1, below:

EXAMPLE 16

Inhibition of Tyrosine-Specific Protein Phosphorylation

Example 16, summarized in Table 3, below, illustrates the capacity of Boc-LeuCH$_2$Br to specifically inhibit EGF-mediated tyrosine phosphorylation.

Triton extracts of A-431 cell membranes, prepared substantially as described previously, containing 37.5 μg protein, were labeled with [γ-$^{32}$P] ATP (5 μM, 5 μCi) for 3 minutes at 0° in the presence and absence of Boc-LeuCH$_2$Br (349 nmoles/mg protein). Protein samples were hydrolyzed and phosphoamino acids were separated by the following procedure.

After labeling, membrane proteins were treated with 10% trichloroacetic acid (TCA) containing 10 mM sodium pyrophosphate and 100 μg BSA. After incubation for one hour at 0°, the foregoing mixture was centrifuged at 3,000 rpm and the resulting pellet washed 3 times with 10% TCA/10 mM sodium pyrophosphate. After recentrifugation, the final pellet was washed with ethanol, dried under vacuum, and dissolved in 70 μL of 0.1N NaOH prior to transfer to glass test tubes containing 0.5 mL 6N hydrochloric acid. The tubes were sealed under vacuum and samples were hydrolyzed at 100° for one hour. The resulting hydrolysates were

TABLE 1

| | | | Inhibition of Protein Phosphorylation in A-431 Plasma Membrane Extracts by Peptide Halomethyl Ketones | | | |
|---|---|---|---|---|---|---|
| Example | Compound | Conc. (nmol/mg protein) | No EGF Added (pmol$^{32}$P incorporated/ min/mg protein) | % inhibition | EGF Added (pmol$^{32}$P incorporated/ min/mg protein) | % inhibition |
| Control | — | — | 7.3 | 0 | 20.2 | 0 |
| 1 | Ac-PheGlyAlaLeuCH$_2$Cl | 400 | 5.2 | 29 | 8.3 | 59 |
| 2 | Z-AlaCH$_2$Cl | 400 | 4.1 | 44 | 5.9 | 71 |
| 3 | Boc-LeuCH$_2$Br | 400 | 2.3 | 69 | 7.0 | 65 |
| Control | — | — | 21.6 | 0 | 96.2 | 0 |
| 4 | Boc-LeuCH$_2$Cl | 477 | 11.3 | 48 | 69.0 | 28 |
| 5 | Boc-LeuCH$_2$Br | 477 | 5.6 | 74 | 27.4 | 72 |
| 6 | Boc-TyrCH$_2$Cl | 477 | 7.8 | 64 | 53.0 | 45 |
| 7 | Boc-TyrCH$_2$Br | 477 | 3.6 | 83 | 20.6 | 78 |
| 8 | Boc-ValCH$_2$Cl | 477 | 20.3 | — | 72.2 | 25 |

Examples 9-15, below, illustrate inhibition of protein phosphorylation of the A-431 cell EGF receptor in the presence of EGF. Assays were conducted substantially as described above, except intact A-431 cell membranes were employed, rather than solubilized extracts, and assay mixtures contained 1 mM ouabain. In these Examples, reactions were permitted to proceed for 6 minutes. This technique is substantially similar to that disclosed by Navarro et al., *Biochemistry*, 21:6138 (1982). The results of these experiments are set forth in Table 2, below:

TABLE 2

Inhibition of Protein Phosphorylation of A-431 Cell Membrane EGF Receptors by Peptide Halomethyl Ketones

| Ex. | Compound | Concentration (nmoles/mg protein) | % inhibition |
|---|---|---|---|
| 9 | Z—Phe-Gly-Ser-LeuCH$_2$Cl | 600 | 54 |
| 10 | Z—Phe-Ser-Ala-LeuCH$_2$Cl | 600 | 44 |
| 11 | Z—Phe-Gly-Ala-TyrCH$_2$Cl | 600 | 67 |
| 12 | Boc-LeuCH$_2$Cl | 600 | 7 |
| 13 | Boc-LeuCH$_2$Br | 600 | 29 |
| 14 | Boc-TyrCH$_2$Cl | 600 | 34 |
| 15 | Boc-TyrCH$_2$Br | 600 | 49 | lyophilized, resuspended in 30 μL water and electrophoresed on Whatman 3MM paper for 3 hours at 3,000 V, at pH 3.5 in 5% acetic acid/0.5% pyridine. Phosphotyrosine, phosphoserine, and phosphothreonine (10 μg of each) were employed as markers. Following electrophoresis, spots corresponding to the foregoing phosphoamino acids were located by ninhydrin treatment, excised, and bleached with 6% hydrogen peroxide. Radioactivity of the spots was determined by scintillation counting and expressed as cpm. Total phosphoprotein of a 1/7 aliquot of each reaction mixture was determined as previously described. Results of these experiments, set forth in Table 3, below, demonstrate the pronounced inhibition of tyrosine phosphorylation attributable to Boc-LeuCH$_2$Br in both the presence and absence of EGF.

TABLE 3

Specific Inhibition of Tyrosine Phosphorylation by Boc-LeuCH$_2$Br

| | EGF Absent | | EGF Present | |
|---|---|---|---|---|
| P—amino Acid | Control | Boc-LeuCH$_2$Br | Control | Boc-LeuCH$_2$Br |
| P—tyrosine | 1152 | 488 | 18000 | 5554 |
| P—threonine | 1100 | 1180 | 1994 | 1270 |
| P—serine | 328 | 300 | 494 | 262 |

TABLE 3-continued

Specific Inhibition of Tyrosine Phosphorylation by Boc-LeuCH$_2$Br

| P—amino | EGF Absent | | EGF Present | |
|---|---|---|---|---|
| Acid | Control | Boc-LeuCH$_2$Br | Control | Boc-LeuCH$_2$Br |
| Total Phosphoprotein | 3408 | 2024 | 12204 | 5332 |

EXAMPLE 17

Boc-LeuCH$_2$Br Inhibition of Protein Phosphorylation by Immunoprecipitates of Cells Transformed by RSV and Fujinami Sarcoma Virus (FSV)

In this experiment, Boc-LeuCH$_2$Br was tested as an inhibitor of pp60$^{src}$ and p130$^{fps}$, the tyrosine-specific protein kinases encoded by the transforming genes of RSV and Fujinami sarcoma virus, respectively.

These viral gene products were partially purified by preparation of immune complexes substantially according to the technique described by Collett et al., Proc. Nat. Acad. Sci. USA 75:2021 (1978). In this procedure, immunoprecipitates are prepared by incubation of extracts of virus-transformed cells with tumor-bearing rabbit serum (TBR) and Staphylococcus protein A suspension (for RSV-transformed cells) or anti-gag serum and Staphylococcus protein A suspension (for FSV-transformed cells).

Assay mixtures contained, in a final volume of 70 μL, 100 μg of immune complex protein, 20 mM Hepes, pH 7.4, and 1 mM MnCl$_2$. Phosphorylation was initiated by addition of 1 μM (4 μCi) [γ-$^{32}$P] ATP. After 10 minutes at about 23°, reactions were terminated by pipetting 20 μL aliquots of assay mixture onto 2×2 cm squares of Whatman 3 MM filter paper, which were immediately suspended in 10% TCA/10 mM sodium pyrophosphate. Test mixtures contained 250 nmoles Boc-LeuCH$_2$Br per mg protein. Controls for the immunoprecipitation procedure were prepared by immunoprecipitating transformed cell extracts with normal serum. The results are set forth in Table 4, below. Values in parentheses represent specific phosphorylation induced by virus-transformed cells.

In a related experiment, the capacity of Boc-LeuCH$_2$Br to inhibit phosphorylation of casein by p130$^{fps}$ was determined. These tests were conducted substantially as described above, except 1 mg/mL casein was added to assay mixtures as a substrate, and reactions were terminated by addition of 2.5 mM unlabeled ATP and immediate cooling to 0°. Phosphorylated casein was separated from immunoprecipitate suspensions by centrifugation at 3,000 xg for 3 minutes. The resulting pellets were resuspended in 70 μL of 10 mM Hepes, pH 7.5, and 20 μL aliquots were pipetted onto filter paper squares as previously described. Results are set forth in Table 4, below:

TABLE 4

Inhibition of RSV and Fujinami Sarcoma Virus Transforming Gene Products (pp 60$^{src}$ and p 130$^{fps}$) by Boc-LeuCH$_2$Br

| | Immune Complex Phosphorylation | | Casein Phosphorylaton | |
|---|---|---|---|---|
| | No inhibitor$^{(cpm)}$ | Boc-LeuCH$_2$Br | No inhibitor$^{(cpm)}$ | Boc-LeuCH$_2$Br |
| pp$^{60}$ + control serum | 7872 | 7516 | | |
| pp60$^{src}$ + TBR serum | 12984(5112) | 10718(3202) | | |
| p130$^{fps}$ + control serum | 9140 | 8898 | | |
| p130$^{fps}$ + anti-gag serum | 29244(20104) | 15222(6324) | | |
| p130$^{fps}$ + control serum | 1184 | 1286 | 326 | 226 |
| p130$^{fps}$ + anti-gag serum | 7663 | 1656 | 4442 | 618 |

EXAMPLE 18

Inhibition of Fujinami Sarcoma Virus (FSV) Transforming Gene Product by Boc-LeuCH$_2$Br and Boc-TyrCH$_2$Br This experiment was conducted substantially according to the procedures described in Example 17, above. Results are set forth in Table 5, below. In Table 5, "FSV" refers to immunoprecipitates of FSV-transformed cell extracts prepared by addition of anti-gag serum; controls were extracts immunoprecipitated with normal serum.

TABLE 5

| | Conc. (nmoles/mg protein) | Activity (cpm) | | % Inhibition |
|---|---|---|---|---|
| Inhibitor | | Control | FSV | |
| none | — | 2624 | 27036 | 0 |
| Boc-LeuCH$_2$Br | 250 | 2370 | 13932 | 48 |
| | 500 | 2180 | 8344 | 69 |
| Boc-TyrCH$_2$Br | 250 | 2132 | 4204 | 84 |
| | 500 | 2140 | 3404 | 87 |

EXAMPLES 19-30

Inhibition of Casein-Phosphorylating Activity of FSV Transforming Gene Product by Peptide Halomethyl Ketones In these experiments, the inhibiting capacity of various peptide chloromethyl ketones was tested against p130$^{fps}$, substantially as described in Examples 17 and 18, above. Results are set forth in Table 6, below:

TABLE 6

| Example | Compound | Percent Inhibition |
|---|---|---|
| 19 | Boc-LeuCH$_2$Br | 63 |
| 20 | Z—Phe-Gly-Ala-LeuCH$_2$Cl | 27 |
| 21 | Ac-Phe-Gly-Glu-LeuCH$_2$Cl | 0 |
| 22 | Ac-Phe-Glu-Ala-LeuCH$_2$Cl | −1 |
| 23 | Z—Phe-Gly-Phe-LeuCH$_2$Cl | 34 |
| 24 | Z—Phe-Phe-Ala-LeuCH$_2$Cl | 11 |
| 25 | Z—Phe-Gly-Pro-LeuCH$_2$Cl | 7 |
| 26 | Z—Phe-Pro-Ala-LeuCH$_2$Cl | 16 |
| 27 | Z—Phe-Gly-Leu-LeuCH$_2$Cl | 44 |
| 28 | Z—Phe-Leu-Ala-LeuCH$_2$Cl | 36 |
| 29 | Z—Phe-Gly-Lys-LeuCH$_2$Cl | 48 |

TABLE 6-continued

| Example | Compound | Percent Inhibition |
|---|---|---|
| 30 | Z—Phe-Lys-Ala-LeuCH$_2$Cl | 11 |

EXAMPLES 31–36

Inhibition of Tumor Cell Line Growth by Peptide Halomethyl Ketones

In this series of experiments, the tumor cell growth inhibitory capacity of various peptide halomethyl ketones was tested against lymphoma cell lines YAC-1 and MOLT-4, and against an erythroleukemia cell line, K-562. The lymphoma cell line YAC-1 is described by Kiessling, et al., *Eur. J. Immunol.* 5:112 (1975), and MOLT-4 is described by Minowada, et al., *J. Natl. Cancer Inst.* 49:891 (1972) and Nilsson, et al., *Int. J. Cancer* 15:321 (1975). The erythroleukemia cell line K-562 is described by Lozzio, et al., *Leuk. Res.* 3:363 (1979). In these experiments, cells were grown on standard media as 10 mL suspension cultures. Initial cell density was 10$^5$ cells/mL. At day 0, test compounds were introduced in ethanol; control cultures received an equal volume of ethanol. Cells were counted at the times indicated. Results, expressed as percentage of cells present in test cultures relative to control cultures, are set forth in Tables 7–12, below:

TABLE 7

Inhibition of Tumor Cell Growth by Boc-LeuCH$_2$Br (Example 31)

| Dose (μg/mL) | % Growth Relative to Control Cultures Day | | | | |
|---|---|---|---|---|---|
| | 1 | 2 | 3 | 4 | 7 |
| | YAC-1 | | | | |
| 0.4 | | | | 97 | |
| 2.0 | 42 | 31 | 28 | 12 | 28 |
| 10. | 67 | 32 | 22 | 13 | 16 |
| | MOLT-4 | | | | |
| 0.4 | | 66 | 84 | 67 | |
| 2.0 | | 29 | 31 | 21 | 74 |
| 10. | 49 | 16 | 14 | 9 | 14 |
| | K-562 | | | | |
| 0.4 | | | 70 | | 85 |
| 2.0 | 53 | 22 | 19 | 16 | 69 |
| 10. | 33 | 22 | 7 | 17 | 13 |

TABLE 8

Inhibition of Tumor Cell Growth by Boc-LeuCH$_2$Cl (Example 32)

| Dose (μg/mL) | % Growth Relative to Control Cultures Day | | | | |
|---|---|---|---|---|---|
| | 1 | 2 | 3 | 4 | 7 |
| | MOLT-4 | | | | |
| 0.4 | 73 | 86 | 73 | | 86 |
| 2.0 | 47 | 28 | 10 | 11 | 63 |
| 10. | | 38 | 3 | 3 | 4 |
| | K-562 | | | | |
| 0.4 | 47 | | 53 | | |
| 2.0 | 17 | 31 | 8 | 15 | 37 |
| 10. | 8 | 17 | 3 | 6 | 3 |

TABLE 9

Inhibition of Tumor Cell Growth by Boc-TyrCH$_2$Cl (Example 33)

| Dose (μg/mL) | % Growth Relative to Control Cultures Day | | | | |
|---|---|---|---|---|---|
| | 1 | 2 | 3 | 4 | 7 |
| | MOLT-4 | | | | |
| 0.4 | 80 | | 85 | 69 | |
| 2.0 | 56 | 31 | 17 | 16 | 31 |
| 10. | 39 | 19 | 8 | 3 | 0 |
| | K-562 | | | | |
| 2.0 | 81 | 23 | 15 | 19 | 44 |
| 10. | 64 | 7 | 2 | 2 | 0 |

TABLE 10

Inhibition of Tumor Cell Growth by Z—Phe-Ser-Ala-LeuCH$_2$Cl (Example 34)

| Dose (μg/mL) | % Growth Relative to Control Cultures Day | | | | |
|---|---|---|---|---|---|
| | 1 | 2 | 3 | 4 | 7 |
| | YAC-1 | | | | |
| 0.4 | 58 | 49 | | | |
| 2.0 | 53 | 53 | | | 76 |
| 10. | 63 | 21 | 16 | 16 | 17 |
| | MOLT-4 | | | | |
| 0.4 | | 80 | | | |
| 2.0 | | 85 | | | |
| 10. | 64 | 16 | 4 | 2 | 11 |
| | K-562 | | | | |
| 0.4 | 82 | 66 | | | |
| 2.0 | | 72 | | | |
| 10. | 44 | 4 | 2 | 4 | 7 |

TABLE 11

Inhibition of Tumor Cell Growth by Z—Phe-Gly-Ser-LeuCH$_2$Cl (Example 35)

| Dose (μg/mL) | % Growth Relative to Control Cultures Day | | | | |
|---|---|---|---|---|---|
| | 1 | 2 | 3 | 4 | 7 |
| | YAC-1 | | | | |
| 0.4 | | 63 | 68 | 74 | 61 |
| 2.0 | | 80 | 60 | 66 | 75 |
| 10. | 62 | 40 | | 40 | 64 |
| | MOLT-4 | | | | |
| 0.4 | 77 | 40 | | | |
| 2.0 | 42 | 27 | 87 | 74 | |
| 10. | 38 | 17 | 76 | 29 | 49 |
| | K-562 | | | | |
| 0.4 | | 28 | 27 | 49 | 81 |
| 2.0 | 66 | 13 | 38 | 40 | |
| 10. | | 14 | 17 | 20 | 65 |

TABLE 12

Inhibition of Tumor Cell Growth by Ac-Phe-Gly-Ala-LeuCH$_2$Cl (Example 36)

| Dose (μg/mL) | % Growth Relative to Control Cultures Day | | | | |
|---|---|---|---|---|---|
| | 1 | 2 | 3 | 4 | 7 |
| | YAC-1 | | | | |
| 0.4 | 80 | 91 | | | |
| 2.0 | | | | | |
| 10. | 78 | 59 | 43 | 24 | |
| | MOLT-4 | | | | |
| 0.4 | 50 | | | 72 | 66 |
| 2.0 | | | | 87 | |
| 10. | | | | | 88 |
| | K-562 | | | | |

TABLE 12-continued
Inhibition of Tumor Cell Growth
by Ac-Phe-Gly-Ala-LeuCH₂Cl
(Example 36)

| Dose (μg/mL) | % Growth Relative to Control Cultures Day | | | | |
|---|---|---|---|---|---|
|  | 1 | 2 | 3 | 4 | 7 |
| 0.4 | 81 |  | 85 |  | 84 |
| 2.0 |  |  |  | 79 |  |
| 10. |  | 77 | 87 |  | 47 |

What is claimed is:

1. A process for inhibiting the growth of tumor cells in a medium, comprising contacting the cells with an effective amount of a compound of the formula

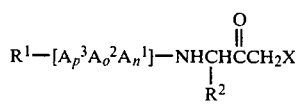

or a physiologically acceptable salt thereof, wherein
  $R^1$ is hydrogen or an N-terminal protecting group;
  $R^2$ is methyl, isopropyl, isobutyl, or 4-hydroxybenzyl;
  $A^1$ is an amino acid residue selected from the group consisting of Phe, Ser, Leu, Lys and Ala;
  $A^2$ and $A^3$ are independently selected from the group consisting of Phe, Gly, Ala, Pro, Leu, Lys, or Ser;
  X is Cl or Br; and
  N, o and p are each 1.

2. A process according to claim 1, wherein $R^1$ is an arylcarbonyl, alkylcarbonyl, alkoxycarbonyl, aryloxycarbonyl, aralkoxycarbonyl, arylsulfonyl, or arylsulfenyl protecting group.

3. A process according to claim 2, wherein $R^2$ is isobutyl or 4-hydroxybenzyl.

4. A process according to claim 3, wherein
  $R^1$ is Z;
  $R^2$ is isobutyl or 4-hydroxybenzyl;
  $A^1$ is Lys or Ala;
  $A^2$ is Gly;
  $A^3$ is Phe; and
  X is Cl.

* * * * *